United States Patent [19]

Yuhas

[11] 4,322,400

[45] Mar. 30, 1982

[54] COSMETIC STICK COMPOSITION

[75] Inventor: Edward R. Yuhas, Yonkers, N.Y.

[73] Assignee: Dragoco Inc., Totowa, N.J.

[21] Appl. No.: 76,663

[22] Filed: Sep. 18, 1979

Related U.S. Application Data

[63] Continuation-in-part of Ser. No. 971,113, Dec. 19, 1978, Pat. No. 4,226,889.

[51] Int. Cl.$^3$ .......................... A61K 7/42; A61K 7/44; A61K 31/055; A61K 7/021
[52] U.S. Cl. .................................. 424/59; 252/522 A; 424/DIG. 5; 424/DIG. 10; 424/DIG. 13; 424/60; 424/63; 424/64; 424/65; 424/67; 424/68; 424/145; 424/347; 424/357; 424/358; 424/361
[58] Field of Search ............................ 424/65, DIG. 5

[56] References Cited

U.S. PATENT DOCUMENTS

| | | | |
|---|---|---|---|
| 2,890,987 | 6/1959 | Hilfer | 424/DIG. 5 |
| 2,970,083 | 1/1961 | Bell | 424/DIG. 5 |
| 3,255,082 | 6/1966 | Barton | 424/DIG. 5 |
| 3,574,854 | 4/1971 | Bassard | 424/168 |
| 3,708,435 | 1/1973 | Starkman | 424/168 |

*Primary Examiner*—Dale R. Ore
*Attorney, Agent, or Firm*—Kenyon & Kenyon

[57] ABSTRACT

Solid, stick-type cosmetic compositions consist essentially of from about 1 to about 30 parts by weight of sodium stearate, 100 parts by weight of water and an "active" material intended to be applied to the skin. The composition also preferably contains a polyhydroxyl compound, such as a glycol or a polyglycol in an amount of from about 0.5 to about 10 weight percent. The addition of up to about 5 weight percent sodium chloride reduces the "syneresis" effect upon storing the compositions at low or high temperature, and increases the setting point of the composition. The compositions are useful as deodorant sticks, perfume sticks, sun sticks, hand lotion sticks, talc sticks, pigment sticks and insect repellant sticks.

27 Claims, No Drawings

COSMETIC STICK COMPOSITION

RELATED APPLICATIONS

This application is a continuation-in-part of copending application Ser. No. 971,113 filed Dec. 19, 1978, now U.S. Pat. No. 4,226,889.

The present invention is concerned with stick-type cosmetic compositions. More specifically, the present invention relates to inexpensive stick-type cosmetic compositions.

BACKGROUND

The use of cosmetic preparations in stick form is well known. These preparations have varied from stick-type deodorants and antiperspirants to lipsticks to compressed cosmetic powder sticks. Depending upon the specific application, the vehicle employed in a stick-type cosmetic can vary greatly.

For example, stick-type deodorant compositions typically consist of a bacteriostat or other biologically active compound dispersed in a vehicle comprising an alcohol-based gel containing either ethanol or a glycol such as propylene glycol, as the vehicle base. In either case, gelation is effected by use of a soap, e.g., sodium stearate, as the gelling agent. These stick-type deodorants may also contain small amounts of other additives, such as perfumes, humectants, various surfactants, dyes or other colorants, water, etc. Both types of formulation have left something to be desired. For example, the ethanol in the ethanol-based product is relatively volatile and can evaporate on storage, especially at elevated temperatures. As a consequence, the stick shrinks and becomes mis-shapen and generally useless. The glycol-based deodorant sticks do not suffer from this disadvantage; however, glycols provide a product which is hard and waxy, and thus has an undesirable "feel" and/or little covering power.

Lipsticks and similar cosmetic products, on the other hand, typically employ fats and/or waxes, such as castor oil, carnauba wax, candelia wax, beeswax, and the like. Vehicles of this type are relatively expensive, and in many cases cannot be employed in the formulation of other cosmetic products.

Powder sticks have been formed by compression of the powder; however, such products are generally so hard that it is difficult to deposit sufficient powder when the compressed powder is applied to the skin of the user. As a consequence, various solutions have been proposed, such as reducing the degree of compression, coupled with providing the composition with a separate wrapper or a dry film to prevent "shedding" of the loosely compacted powder. See, e.g., U.S. Pat. No. 3,471,611. In another effort, the use of gums or other materials as adhesive binders have been described in U.S. Pat. No. 3,800,034. Such efforts have not been particularly successful, and by increasing the number of manufacturing steps, necessarily increase cost of manufacture of the product.

DESCRIPTION OF THE INVENTION

It is an object of this invention to provide an improved cosmetic stick composition.

It is a further object of this invention to provide a new, low cost vehicle base for cosmetic stick compositions.

A further object of this invention is to provide a new vehicle capable of use in cosmetic stick compositions having a variety of uses.

Still another object of this invention is to provide a vehicle suitable for use in deodorant sticks, lipsticks, talc sticks and other cosmetic stick applications.

These and other objects of this invention, which will be apparent from the ensuing specification and claims, are achieved by a solid composition consisting essentially of water, sodium stearate and one or more "active" ingredients intended to be deposited on human skin.

The basic vehicle of the composition of this invention is a mixture of water and sodium stearate in proportions sufficient to form a self-supporting solid composition which does not readily deform and yet is not so firm that a hard, waxy composition results which will not leave a deposit of the "active" ingredient on skin to which the composition is applied. In general, suitable products are obtained when the proportion of sodium stearate is in the range of from about 1 to about 30 parts by weight per 100 parts of water. Preferred compositions ordinarily are obtained when the amount of sodium stearate is from about 2 to about 20 parts per 100 parts of water. Of course, the optimum proportion of sodium stearate to water in any particular instance will depend upon the nature of the other ingredients of the cosmetic stick composition. Nonetheless, most useful compositions will have proportions of sodium stearate to water within the above ranges.

The third essential ingredient of the cosmetic stick composition of this invention is an "active ingredient", by which is meant an ingredient which it is desired to deposit on the skin of a human being. Such active ingredients can include biologically active materials such as bacteriostats and fungistats, pigments and dyes or other colorants, perfumes, emollients, ultraviolet absorbers or "sun screens", and talc. Of course, any active ingredient must be stable in the aqueous alkaline environment provided by the sodium stearate-water vehicle. Consequently, antiperspirant materials, such as aluminum chlorohydrate and related materials cannot be employed in the present invention. Depending upon the intended end use of the cosmetic stick composition, the amount of the "active ingredient" can vary from as little as 0.05 weight percent or less up to 50 weight percent or more of the total weight of the composition.

The composition of this invention can be employed to form a deodorant stick composition, wherein the active ingredient is a bacteriostat. Suitable bacteriostats include 2,2'-methylene-bis(3,4,6-trichlorophenol), 2,4,4'-trichloro-2'-hydroxy(diphenyl ether), zinc phenolsulfonate, 2,2'-thiobis(4,6-dichlorophenol), p-chloro-m-xylenol, dichloro-m-xylenol and the like. In such deodorant stick compositions, the proportion of sodium stearate is desirably from about 2 to about 15, and preferably from about 9 to about 12, parts per 100 parts of water. The proportion of bacteriostat is an amount sufficient to act as a deodorant, i.e., to provide a deposit on skin to which the composition is applied which is effective to inhibit the growth of bacteria. Such amounts ordinarily are in the range of from about 0.05 to about 0.5 weight percent, and preferably from about 0.075 to about 0.2 weight percent, of the total composition.

Perfume sticks based upon the stearate-water system can be prepared by including one or more aromatic substances into the composition. These aromatic substances may include natural products such as essential oils, flower oils, natural extracts from resins, gums, balsams, beans, mosses and other plants, and animal fixtures such as ambergris and musk, as well as synthetic aromatic materials. The variety of such materials is too great to list. Suffice it to say that they generally fall into several well known categories, such as the floral, the spicy, the woody, the chypre or mossy, the oriental, the herbal, the leather-tobacco and the aldehydic groups. Men's fragrances can be classified into the citrus, the spice, the leather, the lavender, the fougere, and the woody groups. Typically, fragrance materials are supplied as concentrates which generally contain from about 0.5 to about 20 percent, and more usually contain from about 3 to about 12 percent of one or more fragrance compounds in a solvent such as water or alcohol. In forming a perfume stick composition from such concentrates, the proportion of sodium stearate is from about 5 to about 15, and preferably from about 10 to about 12, parts per 100 parts of water, and the amount of fragrance concentrate is from about 2 to about 8, and preferably from about 3 to about 5, weight percent of the total composition.

Many perfume oils are incompatible with an aqueous system, especially when employed in large amounts in such products as deodorants colognes. When an attempt is made to use such oils in a stick-type composition of this invention, the result is a soft, mushy composition. In the past, this incompatability problem has been overcome by the use of surfactants to form an emulsion of the perfume oil in the aqueous medium. While this solution has proven satisfactory if the cosmetic product is a liquid product, it has been found to be unavailing in forming stick-type products, such as a stick-type deodorant cologne, in accordance with this invention. The perfume oil emulsion interferes with the setting of the sodium stearate-water vehicle, and rather than forming a solid stick, a soft, cream-like composition is obtained. This can be counteracted, in part, by increasing the amount of sodium stearate, but this leads to a hardy waxy product which has undersirable "feel". It has been found, however, that good quality, solid, stick-type products, such as stick cologne deodorants, can be obtained if the fragrance oil is first formulated as a fragrance concentrate wherein the essential oil is dissolved in a glycol or a diglycol, wherein the amount of oil does not exceed 50 weight percent of the concentrate. Suitable glycols are those containing from about 2 to about 6 carbons, such as ethylene glycol, propylene glycol, butylene glycol, and hexylene glycol. The diglycols which can be employed are the diglycols of glycols containing from about 2 to about 6 carbons, for example, diethylene glycol and dipropylene glycol. The fragrance concentrate can then be admixed with the remaining ingredients of the stick-type composition.

Another type of stick-type cosmetic product which may be prepared in accordance with this invention is a sun stick, in which the active ingredient is an ultraviolet absorber such as p-aminobenzoic acid, its salts or its esters, as well as N-substituted derivatives such as p-(dimethylamino) benzoic acid, an anthranilate, a salicylate, esters of cinnamic acid, dihydroxycinnamic acid or trihydroxycinnamic acid, diphenyl-butadiene, stilbene, a napthol sulfonate, a coumarin derivative, a quinine salt, a quinoline derivative, hydroquinone, tannic acid, zinc oxide, dioxybenzone and oxybenzone. In such compositions, the sodium stearate is present in an amount of from about 5 to about 15, and preferably from about 10 to about 12, parts by weight per 100 parts of water, and the ultraviolet absorber or screen is present in an amount of from about 0.5 to about 5 percent, and preferably from about 1 to about 4 percent of the total weight of the composition.

Still another cosmetic stick composition within the scope of this invention is an emollient and lubricating composition wherein the "active ingredient" is a water compatible humectant or emollient composition. Such a composition includes sugar derivatives, for example sucrose and glucose which have been esterified with long chain fatty acids such as stearic acid, e.g., sucrose monostearate, and/or sucrose distearate, and glucose derivatives such as methyl glucoside sesquistearate as well as ethoxylated and propoxylated sugars such as ethoxylated methyl glucose sesquistearate and propoxylated glucose. In such compositions, the sodium stearate is employed in an amount of from about 5 to about 15 parts, and preferably from about 10 to about 12 parts per 100 parts water, and the humectant and/or emollient is employed in an amount of from about 2 to about 10, and preferably from about 4 to about 8 percent of the weight of the total composition.

The compositions of this invention also comprise make-up sticks, in which a solid pigment to be applied as a rouge, lipstick, eye-shadow, eye-liner, etc., is incorporated into the composition as the active ingredient. The pigments include titanium dioxide, zinc oxide, iron oxide and the like, aluminum lake, barium lake, calcium lake, strontium lake, tetrabromofluorescein, tetrabromotetrachlorofluorescein, dibromofluorescein and the like. In such compositions, the amount of sodium stearate is from about 5 to about 15, and preferably from about 9 to about 12 parts per 100 parts of water, and the amount of pigment is from about 1 to about 10 percent, and preferably from about .3 to about 8 percent, based on the total weight of the composition.

A further specific cosmetic formulation embodying the present invention comprises a solid talc stick, in which the "active ingredient" is powdered cosmetic grade talc, which typically has particles whose sizes are about 200 mesh or less, and more specifically are in the range of from about 200 to about 400 mesh (U.S. Standard Series). In such a composition, the amount of sodium stearate can vary from about 1 to about 30, and preferably from about 8 to about 20 parts per 100 parts of water, and the amount of talc can vary from about 10 to about 100, and preferably from about 10 to about 50 parts per 100 parts of water.

It also is within the scope of this invention that two or more active substances can be present. For example, a talc stick can also include a bacteriostat and/or a fungistat for use as a medicated powder stick, for example a foot powder stick, or it can contain a pigment for use as a pigmented talc stick.

Apart from the sodium stearate, water and "active ingredient," the cosmetic stick composition of this invention may contain small amounts of ingredients intended primarily to modify the properties of the stick compositions, and not for deposit on human skin. In particular, it is highly desirable to include relatively small amounts of water compatible polyhydroxyl compound, e.g. glycerine, a glycol or a polyglycol, to modify the physical properties of the composition and impart an improved "feel". Suitable glycols and polyglycols include glycols having at least 2 carbons and preferably from about 3 to about 6 carbons, such as propylene glycol, butylene glycol, and hexylene glycol, and polyglycols such as polyethylene and polypropylene glycols having molecular weights of up to about 25,000, such as dipropylene glycol, and polyethylene glycols having molecular weights in the range of from about 150 to about 25,000 and the like. The glycols and the lower molecular weight polyglycols, i.e., those having molecular weights of below about 10,000 are useful in providing a composition which is somewhat softer, and aid in promoting deposition of the "active" ingredient onto the skin of the user. The higher molecular weight polyglycols, for example a polyethylene glycol sold by Union Carbide Corp as "Carbowax 20M", in contrast can be employed to provide increased hardness. Their use permits the formulation of stick-type cosmetic products containing up to about 95 weight percent water. When employed, the glycol compound comprises from about 0.5 to about 10 weight percent, and preferably from about 1 to about 8 weight percent of the total cosmetic stick composition.

Still other components of the talc stick are odorants and colorants, which are primarily intended to impart a color or fragrance to the stick composition. By the term "odorant", as employed herein, is meant an additive such as a perfume which give the composition a desired odor, as well as an odor mask, which is intended to mask the characteristic odors of other ingredients and thus provide an "unscented" product. By the term "colorant", as employed herein, is meant a dye or other agent employed to impart a particular color to or to mask a particular color of the deodorant stick composition. Ordinarily, such additives will comprise from about 0.1 to about 1 weight percent of the cosmetic stick composition.

When the cosmetic stick composition of this invention is subjected to temperature extremes, e.g., a temperature as low as about 0° to 40° C., or a temperature of about 50° C. or higher, it has been found that water exudes from the solid stick. Attempts to prevent such "syneresis" through the use of increased amounts of sodium stearate have not proven to be particularly successful because a hard, waxy composition results. This can be counteracted by increasing the amount of polyhydrox compound in the composition, but the increased proportions of both ingredients results in a more costly product. It has been further found, however, that the addition of relatively small amounts of sodium chloride to the composition materially reduces the syneresis effect. It also has been found that the addition of sodium chloride increases the settling point, as well as the rate of setting, of the water-sodium stearate cosmetic stick base of this invention. Thus, stick-type cologne compositions which otherwise might be too soft for practical use in a stick-type product, such as deodorant colognes containing high proportions of perfume oils, can be formulated into a cosmetic stick composition by the use of sodium chloride.

The amount of sodium chloride, when employed, should be balanced with the amount of sodium stearate so that the setting point of the composition is in the range of from about 50° C. to about 60° C., and preferably is from about 53° C. to about 57° C., and optimally is at about 55° C. The specific amounts of sodium chloride and sodium stearate which may be used in any specific composition are readily determined through routine experimentation. In general, however, when sodium chloride is employed, it will usually be employed in an amount of at least about 0.5 weight percent, and preferably at least about 1 weight percent, and satisfactory results are obtained using amounts of sodium chloride of up to about 5 weight percent, based upon the water-sodium stearate vehicle, with amounts of from about 1.5 to about 2.5 weight percent being preferred. It also is desired that the weight of sodium chloride employed be not greater than the weight of sodium stearate; i.e., that the weight ratio of sodium chloride to sodium stearate be no greater than about 1:1.

Preferred cosmetic stick compositions of this invention generally contain at least 90 weight percent active ingredient, sodium stearate and water, with the balance (10 weight percent or less) being polyhydroxyl compound and odorant or colorant.

The composition of this invention is formed by mixing the ingredients at elevated temperatures sufficient to form a liquid solution or suspension, ordinarily about 70° to about 85° C., pouring the liquid into a mold or dispensing container and allowing it to cool and set. In some cases, a period of several hours or even days may be required before the cosmetic stick composition is completely solidified. It is preferred that the water and sodium stearate, and optionally the other liquid or liquifiable ingredients, be first mixed to form a clear solution, and the solid ingredients such as talc or pigments are then added. The mixture is then partially cooled, at which time volatile components, such as perfume oils, are added, and then final cooling is effected.

The following examples are illustrative.

EXAMPLE 1

Deodorant Stick Formulations

A series of six compositions was prepared containing from 0.5 to 20 parts by weight of sodium stearate, 93 to 73.5 parts by weight of water, 6 parts by weight of propylene glycol, 0.1 part by weight of 2,4,4'-trichloro-2'-hydroxy(diphenyl ether) (THDE), and 0.4 parts by weight of perfume. For each composition, all ingredients but the perfume were heated at 70°–75° C. with stirring until a clear solution was formed. The solution was cooled to 60°–65° C. and the perfume was added. The resulting solution was then poured into a dispensing container and allowed to cool and set. Each of the compositions was then examined for consistency. The results are summarized below.

| Components, wt. % | Deodorant Composition | | | | | |
|---|---|---|---|---|---|---|
| | A | B | C | D | E | F |
| Sodium stearate | 0.5 | 1.0 | 4.0 | 8.5 | 10.0 | 20.0 |
| Water | 93.0 | 92.5 | 89.5 | 86.0 | 83.5 | 73.5 |
| Propylene glycol | 6.0 | 6.0 | 6.0 | 6.0 | 6.0 | 6.0 |
| THDE | 0.1 | 0.1 | 0.1 | 0.1 | 0.1 | 0.1 |
| Perfume | 0.4 | 0.4 | 0.4 | 0.4 | 0.4 | 0.4 |
| Evaluation: | Watery and soft | Watery and soft | Solid, with wet | Smooth, hard stick | Smooth, hard stick | Very hard, waxy |

| Components, | Deodorant Composition | | | | | |
|---|---|---|---|---|---|---|
| wt. % | A | B | C | D | E | F |
| | | | surface | which leaves good deposit on skin | which leaves good deposit on skin | "candle" with no "payoff" |

Of the formulations tested, compositions D and E containing 8.5 and 10 percent sodium stearate provided the best balance of properties.

EXAMPLE 2

Deodorant Stick Formulation

A mixture of 8.5 parts by weight of sodium stearate, 6 parts by weight of propylene glycol, and 84 parts by weight of water was heated to 70°–75° C. with constant stirring until a clear solution was formed. The composition was then cooled to 60°–65° C. and 1 part by weight of zinc phenol sulfonate and 0.5 part by weight of perfume were added. The resulting composition was poured into a dispensing container and allowed to cool and set. A firm, hard composition was formed which formed a satisfactory deposit of deodorant when applied to human skin.

EXAMPLE 3

Perfume Stick Formulations

Mixtures of 8.5 parts by weight of sodium stearate, 6 parts by weight of propylene glycol, and a perfume concentrate and water in varying proportions were prepared by heating the sodium stearate, propylene glycol and water at 70–75° C., with stirring, until a clear solution was formed. The solution was cooled to 65° C. and the perfume concentrate was added. The resulting mixture was then poured into a dispensing container and allowed to cool and set. Each of the compositions was then examined for consistency. The results are summarized below:

| Components, wt. % | Perfume Stick Composition | | | | | |
|---|---|---|---|---|---|---|
| | A | B | C | D | E | F |
| Sodium stearate | 8.5 | 8.5 | 8.5 | 8.5 | 8.5 | 8.5 |
| Propylene glycol | 6.0 | 6.0 | 6.0 | 6.0 | 6.0 | 6.0 |
| Perfume | 2.0 | 4.0 | 6.0 | 8.0 | 10.0 | 15.0 |
| Water | 83.5 | 81.5 | 79.5 | 77.5 | 75.5 | 70.5 |
| Evaluation: | Firm stick with good odor | Same as A | Same as A | Slightly softer stick | Softer stick | Soft stick |

Based upon the foregoing, compositions containing up to about 8 weight percent of perfume concentrate had sufficient physical integrity to be of practical value as a perfume stick.

EXAMPLE 4

Sun Stick Compositions

A mixture of 8.5 parts of sodium stearate, 6.0 parts of propylene glycol and 82.5 or 84.3 parts of water was heated with stirring at 70°–75° C. until a clear solution was obtained and then either 3.0 or 1.2 parts of an ultra-violet absorber or sun screen was added. The resulting mixture was poured into a dispenser tube and allowed to cool and set to form sun stick compositions having good consistency. The various compositions were as follows:

| Components, wt. % | Sun Stick Composition | | | |
|---|---|---|---|---|
| | A | B | C | D |
| Sodium stearate | 8.5 | 8.5 | 8.5 | 8.5 |
| Propylene glycol | 6.0 | 6.0 | 6.0 | 6.0 |
| Zinc oxide | 3.0 | — | — | — |
| Dioxybenzone | — | 3.0 | — | — |
| Oxybenzone | — | — | 3.0 | — |
| p-(dimethylamino)-benzoic acid | — | — | — | 1.2 |
| Water | 82.5 | 82.5 | 82.5 | 84.3 |

EXAMPLE 5

Humectant Stick Formulations

Mixtures of 8.5 parts by weight of sodium stearate, 85.5 parts by weight of water and 6 parts by weight of certain sugar derivatives sold as humectants by Croda, Inc. under the designation "Crodesta" or by Amerchol under the designations "Glucam", "Glucate" and "Glucamate", were heated with stirring at 70°–75° C. until a clear solution was formed. Each solution was poured into a dispensing container and allowed to set, to form a humectant stick-type product. The formulations were:

| Components, wt. % | Humectant Composition | | | | | |
|---|---|---|---|---|---|---|
| | A | B | C | D | E | F |
| Sodium stearate | 8.5 | 8.5 | 8.5 | 8.5 | 8.5 | 8.5 |
| Sucrose distearate[1] | 6.0 | — | — | — | — | — |
| Sucrose mono- and distearates[2] | — | 6.0 | — | — | — | — |
| Propoxylated (10 moles) glucose[3] | — | — | 6.0 | — | — | — |
| Propoxylated (20 moles) glucose[4] | — | — | — | 6.0 | — | — |
| Methyl glucoside sesquistearate[5] | — | — | — | — | 6.0 | — |
| Ethoxylated (20 moles) methyl glucose sesquistearate[6] | — | — | — | — | — | 6.0 |
| Water | 85.5 | 85.5 | 85.5 | 85.5 | 85.5 | 85.5 |

[1]Sold by Croda, Inc. under the designation Crodesta F 10
[2]Sold by Croda, Inc. under the designation Crodesta F110
[3]Sold by Amerchol under the designation Glucam P 10
[4]Sold by Amerchol under the designation Glucam P 20
[5]Sold by Amerchol under the designation Glucate 55
[6]Sold by Amerchol under the designation Glucamate 55E-20

EXAMPLE 6

Lanolin Stick Formulations

Mixtures of 8.5 parts by weight of sodium stearate, 6.0 parts by weight of propylene glycol, 75.5 parts by weight of water and 10.0 parts by weight of lanolin or commercially available lanolin derivatives were prepared by stirring at 70°–75° C. until a clear solution was obtained, poured into dispensing containers and allowed to cool and set to form lanolin stick formulations useful as solid, stick-form hand creams. The formulations were as follows:

| Components, wt. % | Lanolin Composition | | | | | | | | | | | | |
|---|---|---|---|---|---|---|---|---|---|---|---|---|---|
| | A | B | C | D | E | F | G | H | I | J | K | L | M |
| Sodium stearate | 8.5 | 8.5 | 8.5 | 8.5 | 8.5 | 8.5 | 8.5 | 8.5 | 8.5 | 8.5 | 8.5 | 8.5 | 8.5 |
| Propylene glycol | 6.0 | 6.0 | 6.0 | 6.0 | 6.0 | 6.0 | 6.0 | 6.0 | 6.0 | 6.0 | 6.0 | 6.0 | 6.0 |
| Lanolin, anhyd, USP. | 10.0 | — | — | — | — | — | — | — | — | — | — | — | — |
| Laneto-100[a] | — | 10.0 | — | — | — | — | — | — | — | — | — | — | — |
| Laneto-50[a] | — | — | 10.0 | — | — | — | — | — | — | — | — | — | — |
| Ritachol-5115[a] | — | — | — | 10.0 | — | — | — | — | — | — | — | — | — |
| Super Sat[a] | — | — | — | — | 10.0 | — | — | — | — | — | — | — | — |
| Solulan BP-5[b] | — | — | — | — | — | 10.0 | — | — | — | — | — | — | — |
| Solulan BP 10[b] | — | — | — | — | — | — | 10.0 | — | — | — | — | — | — |
| Solulan C-24[b] | — | — | — | — | — | — | — | 10.0 | — | — | — | — | — |
| Solulan L-575[b] | — | — | — | — | — | — | — | — | 10.0 | — | — | — | — |
| Acetulan[b] | — | — | — | — | — | — | — | — | — | 10.0 | — | — | — |
| Ricilan-B[b] | — | — | — | — | — | — | — | — | — | — | 10.0 | — | — |
| Ricilan-C[b] | — | — | — | — | — | — | — | — | — | — | — | 10.0 | — |
| Viscolan[b] | — | — | — | — | — | — | — | — | — | — | — | — | 10.0 |
| Water | 75.5 | 75.5 | 75.5 | 75.5 | 75.5 | 75.5 | 75.5 | 75.5 | 75.5 | 75.5 | 75.5 | 75.5 | 75.5 |

[a]Laneto, Super Sat and Riachol all are products of Rita Chemical Co.
[b]Acetulan, Solulan, Ricilan and Viscolan all are products of Americol.

All of the compositions were firm solids which were useful as "hand lotions", although compositions A and E had a slightly tacky feel which was not evidenced by the other lanolin stick composition.

EXAMPLE 7

Talc Stick Formulations

A series of seven compositions was prepared by mixing sodium stearate, water, propylene glycol and 2,4,4′-trichloro-2′-hydroxy(dephenyl ether) (THDE) and stirring at 70° to 75° C. The composition was removed from the heat, and talc was stirred in to form a uniform slurry. The slurry was cooled to 60° to 65° C. and perfume was added. The resulting composition were poured into stick-type dispensers and allowed to cool and set. The resulting compositions were then evaluated for physical appearance, form and efficacy in depositing talc. The results are summarized as follows:

| Component, wt. %: | Talc Stick Composition | | | | | | |
|---|---|---|---|---|---|---|---|
| | A | B | C | D | E | F | G |
| Talc | 1.0 | 5.0 | 10.0 | 20.0 | 30.0 | 40.0 | 50.0 |
| Sodium stearate | 8.5 | 8.5 | 8.5 | 8.5 | 8.5 | 8.5 | 8.5 |
| Water | 84.0 | 80.0 | 75.0 | 65.0 | 55.0 | 45.0 | 35.0 |
| Propylene glycol | 6.0 | 6.0 | 6.0 | 6.0 | 6.0 | 6.0 | 6.0 |
| THDE | 0.1 | 0.1 | 0.1 | 0.1 | 0.1 | 0.1 | 0.1 |
| Perfume | 0.4 | 0.4 | 0.4 | 0.4 | 0.4 | 0.4 | 0.4 |

The compositions all were firm solids. However, compositions A and B contained insufficient talc to form a satisfactory deposit when applied to skin. Composition G was too stiff for practical use. Compositions C, D, E and F all provided an adequate deposit of talc when applied to skin. Furthermore, the talc deposit was quite adherent and difficult to rub off the skin. Compositions E and F provided the best balance of properties.

EXAMPLE 8

Talc Stick Formulations

Mixtures of 8.5 parts of sodium stearate, 6.0 parts of a polyethylene glycol, and 55.5 parts of water were stirred at 70°–75° C. The compositions were removed from the heat and talc was stirred in to form a slurry. The resulting compositions were poured into stick-type dispensers and allowed to cool and sit to firm solid talc stick.

| Components, wt. %: | Talc Stick Compositions | | | |
|---|---|---|---|---|
| | A | B | C | D |
| Sodium stearate | 8.5 | 8.5 | 8.5 | 8.5 |
| Polyethylene glycol-200[(1)] | 6.0 | — | — | — |
| Polyethylene glycol-1000[(2)] | — | 6.0 | — | — |
| Polyethylene glycol-4000[(3)] | — | — | 6.0 | — |
| Polyethylene glycol-6000[(4)] | — | — | — | 6.0 |
| Talc | 30.0 | 30.0 | 30.0 | 30.0 |
| Water | 55.5 | 55.5 | 55.5 | 55.5 |

[(1)]Sold by Union Carbide Corp. as Carbowax 200
[(2)]Sold by Union Carbide Corp. as Carbowax 1000
[(3)]Sold by Union Carbide Corp. as Carbowax 4000
[(4)]Sold by Union Carbide Corp. as Carbowax 6000

EXAMPLE 9

Talc Stick Formulation

Talc sticks containing 8.5 parts by weight sodium stearate, 6.0 parts by weight of polyethylene glycol having a molecular weight of about 6000–7500 (Carbowax 6000), from 10 to 45 parts talc and from 75.5 parts to 40.5 parts water were prepared by procedures similar to those described in Example 1.

| Components, wt. %: | Talc Stick Formulation | | | | |
|---|---|---|---|---|---|
| | A | B | C | D | E |
| Sodium stearate | 8.5 | 8.5 | 8.5 | 8.5 | 8.5 |
| "Carbowax 6000" | 6.0 | 6.0 | 6.0 | 6.0 | 6.0 |
| Talc | 10.0 | 20.0 | 30.0 | 40.0 | 45.0 |
| Water | 75.5 | 65.5 | 55.5 | 45.5 | 40.5 |

All talc sticks were solid and firm.

EXAMPLE 10

Pigment Stick Formulations

Employing procedures similar to those described in Example 8, except that brown iron oxide powdered pigment was substituted for or added with talc, three pigment sticks were prepared.

| Components, wt. %: | Pigment Stick Composition | | |
|---|---|---|---|
| | A | B | C |
| Sodium stearate | 12.5 | 12.0 | 8.5 |
| "Carbowax 4000" | 6.0 | 6.0 | — |
| "Carbowax 6000" | — | — | 6.0 |
| Talc | 30.0 | 30.0 | — |
| Pigment | 10.0 | 5.0 | 5.0 |
| Water | 41.5 | 47.0 | 80.5 |

All compositions were solid, dry and left a good deposit pigment when applied to human skin, and were useful as "make up" sticks. The Composition C, containing no talc was somewhat smoother in feel.

EXAMPLE 11

Evaluation of Stearates

A series of mixtures containing 8.5 parts by weight of a stearate, 6.0 parts of propylene glycol, and 85.5 parts of water was prepared by heating with stirring at 70°–75° C. to form a clear solution, pouring into a stick-type dispenser, and cooling to allow the composition to set. The compositions were:

| Components, wt. %: | Stearate Composition | | | | |
|---|---|---|---|---|---|
| | A | B | C | D | E |
| Sodium stearate | 8.5 | — | — | — | — |
| Lithium stearate | — | 8.5 | — | — | — |
| Magnesium stearate | — | — | 8.5 | — | — |
| Zinc stearate | — | — | — | 8.5 | — |
| Aluminum stearate | — | — | — | — | 8.5 |
| Propylene glycol | 6.0 | 6.0 | 6.0 | 6.0 | 6.0 |
| Water | 85.5 | 85.5 | 85.5 | 85.5 | 85.5 |

Of the compositions, all but composition A were extremely soft and totally unsuitable for use as a stick-type cosmetic applicator.

EXAMPLE 12

Evaluation of Glycolic Additives

A series of formulations containing 8.5 parts by weight of sodium stearate, 85.5 parts by weight of a glycolic compound was prepared by procedures described in Example 11. All formed firm solid sticks capable of use in a stick-type cosmetic product.

| Components, wt. % | Composition | | | | | | | | |
|---|---|---|---|---|---|---|---|---|---|
| | A | B | C | D | E | F | G | H | I |
| Sodium stearate | 8.5 | 8.5 | 8.5 | 8.5 | 8.5 | 8.5 | 8.5 | 8.5 | 8.5 |
| Glycerine | 6.0 | — | — | — | — | — | — | — | — |
| Butylene glycol | — | 6.0 | — | — | — | — | — | — | — |
| Hexylene glycol | — | — | 6.0 | — | — | — | — | — | — |
| Triethylene glycol | — | — | — | 6.0 | — | — | — | — | — |
| Dipropylene glycol | — | — | — | — | 6.0 | — | — | — | — |
| Polyethylene(1) glycol-200 | — | — | — | — | — | 6.0 | — | — | — |
| Polyethylene(2) glycol-1000 | — | — | — | — | — | — | 6.0 | — | — |
| Polyethylene(3) glycol-4000 | — | — | — | — | — | — | — | 6.0 | — |
| Polyethylene(4) glycol-6000 | — | — | — | — | — | — | — | — | 6.0 |
| Water | 85.5 | 85.5 | 85.5 | 85.5 | 85.5 | 85.5 | 85.5 | 85.5 | 85.5 |

(1)"Carbowax 200"
(2)"Carbowax 1000"
(3)"Carbowax 4000"
(4)"Carbowax 6000"

Similar results were obtained when the glycolic compound was replaced by 6.0 parts by weight of a high molecular weight alcoholic product sold by Union Carbide Corp. under the general designation "Ucon". Specific products which were employed to form solid stick-type compositions were Ucon L0 500, Ucon 50-HB-260, Ucon 50-HB-660, Ucon 50-HB-5100, Ucon LB-1145 and Ucon LB-1715.

EXAMPLE 13

A series of mixtures of from 2 to 8.5 weight percent sodium stearate, from 81.5 to 96 weight percent water and from 2 to 10 weight percent Carbowax 20 M, a polyethylene glycol having a molecular weight in the range of about 15,000 to 20,000 formed by reaction of 2 moles of Carbowax 6000 with an epoxide, and sold by Union Carbide Corp., was prepared and formed into solid sticks by the procedures described in Example 11. In all cases, firm, solid products capable of use in cosmetic stick-type formulation were obtained.

| Experiment | Composition, weight % | | | |
|---|---|---|---|---|
| | Sodium Stearate | "Carbowax 20 M" | Water | Comment |
| A-1 | 2.0 | 2.0 | 96.0 | Wet, slightly soft solid |
| A-2 | 2.0 | 3.0 | 95.0 | Wet, slightly soft solid |
| A-3 | 2.0 | 4.0 | 94.0 | Wet, slightly soft solid |
| A-4 | 2.0 | 5.0 | 93.0 | Wet, slightly soft solid |
| B-1 | 3.0 | 2.0 | 95.0 | Slightly soft solid |
| B-2 | 3.0 | 3.0 | 94.0 | Slightly soft solid |
| B-3 | 3.0 | 4.0 | 93.0 | Slightly soft solid |
| C-1 | 4.0 | 2.0 | 94.0 | Slightly soft solid |
| C-2 | 4.0 | 3.0 | 93.0 | Slightly soft solid |
| C-3 | 4.0 | 4.0 | 92.0 | Slightly soft solid |
| D-1 | 6.0 | 2.0 | 92.0 | Slightly soft solid |
| E-1 | 8.5 | 0.5 | 91.0 | Slightly hard solid |
| E-2 | 8.5 | 1.0 | 90.5 | Slightly hard solid |
| E-3 | 8.5 | 2.0 | 89.5 | Slightly hard solid |
| E-4 | 8.5 | 4.0 | 87.5 | Slightly hard solid |
| E-5 | 8.5 | 6.0 | 85.5 | Slightly hard solid |
| E-6 | 8.5 | 8.0 | 83.5 | Slightly hard solid |
| E-7 | 8.5 | 10.0 | 81.5 | Slightly hard solid |

From the foregoing, it can be seen that the use of Carbowax 20 M enables the formulation of compositions capable as use as vehicles for solid stick-type cosmetic preparations containing as much as 95 to 96 weight percent water, and as little as 2 weight percent of sodium stearate and the Carbowax 20 M. Compositions having only 2 percent sodium stearate, although slightly soft solids, did have a wet feel which might be undesirable in some applications. This wet feel was eliminated on increasing the sodium stearate content to at least about 3 weight percent. With further increases in the amount of sodium stearate the hardness of the composition increased. At each level of sodium stearate tested, variations in the amount of Carbowax did not appear to materially affect the properties of the product.

EXAMPLE 14

Effect of Sodium Chloride

Employing procedures similar to those described, four stick-type products based on four different formulations containing water, Carbowax 20M and sodium stearate were prepared as follows:

| Components, wt. %: | Formulation | | | |
|---|---|---|---|---|
| | A | B | C | D |
| Water | 95.5 | 90.5 | 85.5 | 80.5 |
| Polyethylene glycol 20M | 2.0 | 4.0 | 6.0 | 8.0 |
| Sodium stearate | 2.5 | 5.5 | 8.5 | 11.5 |

Each of the compositions was then modified by the addition of sodium chloride in amounts of up to 5 weight percent, while reducing the water content by an equal amount, resulting in four series of compositions. Each of the resulting compositions was evaluated for syneresis after storage for from 1 to 3 days in a refrigerator at 4° C. or in an oven at 50° C. In addition, the setting point of each composition was determined, and the setting points are set forth in tabular form below:

| Formulation | Sodium Chloride, wt. % | Setting Point, °C. |
|---|---|---|
| A | 0 | 38.5 |
| A-1 | 1 | 53.5 |
| A-2 | 2 | 58.0 |
| A-3 | 3 | 58.0 |
| A-4 | 4 | Split* |
| A-5 | 5 | 59.0 |
| B | 0 | 42.75 |
| B-1 | 1 | 55.0 |
| B-2 | 2 | 60.5 |
| B-3 | 3 | 59.0 |
| B-4 | 4 | 66.5 |
| B-5 | 5 | 69.5 |
| C | 0 | 46.0 |
| C-1 | 1 | 57.0 |
| C-2 | 2 | 62.5 |
| C-3 | 3 | 65.5 |
| C-4 | 4 | 68.5 |
| C-5 | 5 | 72.0 |
| D | 0 | 48.75 |
| D-1 | 1 | 59.0 |
| D-2 | 2 | 64.0 |
| D-3 | 3 | 68.0 |
| D-4 | 4 | 73.5 |
| D-5 | 5 | 73.5 |

*The formulation split into two phases on stirring and could not be formulated into a homogenous solid.

From the foregoing, it can be seen that adding sodium chloride to the water-based vehicle of this invention results in a marked increase in setting point, and that in each series setting points in the range of 50°–60° C. could be obtained with 1 percent sodium chloride or less. Of particular interest, Formulation A-1, which contained 94.5 percent water, 2.0 percent Carbowax 20M, 2.5 percent sodium stearate and 1 percent sodium chloride, had a setting point of 53.5° C.

The degree of syneresis observed varied inversely with the amount of sodium chloride. All of the basic formulations, when placed in the refrigerator or the oven, exhibited syneresis. In each series, the degree of syneresis was materially reduced by the presence of 1 percent sodium chloride, and for all practical purposes, was essentially eliminated by the presence of 2 percent sodium chloride.

An additional series of experiments was carried out to determine the minimum amount of sodium chloride required to achieve a significant reduction in syneresis and increase in setting point. The basic composition consisted of 4 weight percent each of sodium stearate and Carbowax 20M and 92 weight percent water. As before, sodium chloride was added and the amount of water was reduced by an equal amount. The sodium chloride contents and the setting points of the resulting compositions are summarized as follows:

| Composition | Percent Sodium Chloride | Setting Point, °C. |
|---|---|---|
| 1 | 0 | 40.0 |
| 2 | 0.25 | 42.5 |
| 3 | 0.5 | 47.0 |
| 4 | 1.0 | 51.0 |
| 5 | 1.5 | 54.0 |
| 0 | 2.0 | 58.0 |

Based upon the data presented in this table and the preceding table, it appears that as little as 0.25 weight percent sodium chloride can be effective in increasing the setting point of the cosmetic vehicle of this invention. However, amounts of sodium chloride of at least about 0.5 weight percent, and preferably at least about 1 weight percent, appear necessary to achieve substantial increases in setting point.

EXAMPLE 15

Deodorant Cologne Sticks

Employing procedures similar to those described above, a series of stick-type deodorant colognes containing up to 2 percent perfume were prepared by adding a perfume essential oil to basic Formulations A, B, C and D of Example 14. It was noted that, especially with respect to the series based on Formulation A, the composition became less firm as the amount of perfume oil was increased. In addition, it was found that the setting point of the compositions decreased with increasing perfume oil concentration. Accordingly, additional samples containing sodium chloride were prepared. In all cases, the setting points of the compositions were materially increased by the addition of sodium chloride. The data obtained from this series of experiments is summarized as follows:

| Formulation | Perfume Oil, wt. % | Sodium Chloride, wt. % | Setting Point, °C. |
|---|---|---|---|
| | Basic Formulations | | |
| A | 0 | 0 | 38.5 |
| B | 0 | 0 | 42.75 |
| C | 0 | 0 | 46.0 |
| D | 0 | 0 | 48.75 |
| | 0.2% Perfume Oil | | |
| A Series | 0.2 | 0 | 35.0 |
| | 0.2 | 1 | 50.5 |
| | 0.2 | 2 | 56.0 |
| | 0.2 | 3 | 56.0 |
| | 0.2 | 4 | Split |
| | 0.2 | 5 | 63.5 |
| B Series | 0.2 | 0 | 42.25 |
| | 0.2 | 1 | 54.0 |

| Formulation | Perfume Oil, wt. % | Sodium Chloride, wt. % | Setting Point, °C. |
|---|---|---|---|
| | 0.2 | 2 | 59.0 |
| | 0.2 | 3 | 62.5 |
| | 0.2 | 4 | 66.0 |
| | 0.2 | 5 | 69.0 |
| C Series | 0.2 | 0 | 45.5 |
| | 0.2 | 1 | 56.75 |
| | 0.2 | 2 | 62.0 |
| | 0.2 | 3 | 65.0 |
| | 0.2 | 4 | 69.0 |
| | 0.2 | 5 | 68.5 |
| D Series | 0.2 | 0 | 48.0 |
| | 0.2 | 1 | 59.5 |
| | 0.2 | 2 | 63.0 |
| | 0.2 | 3 | 67.0 |
| | 0.2 | 4 | 73.0 |
| | 0.2 | 5 | 72.0 |
| 0.5% Perfume Oil | | | |
| A Series | 0.5 | 0 | 32.0 |
| | 0.5 | 1 | 45.25 |
| | 0.5 | 2 | 49.0 |
| | 0.5 | 3 | 45.0 (Split) |
| | 0.5 | 4 | Split |
| | 0.5 | 5 | Split |
| B Series | 0.5 | 0 | 41.0 |
| | 0.5 | 1 | 48.0 |
| | 0.5 | 2 | 53.5 |
| | 0.5 | 3 | 56.5 |
| | 0.5 | 4 | 61.0 |
| | 0.5 | 5 | 60.5 |
| C Series | 0.5 | 0 | 44.25 |
| | 0.5 | 1 | 51.5 |
| | 0.5 | 2 | 57.0 |
| | 0.5 | 3 | 59.0 |
| | 0.5 | 4 | 63.0 |
| | 0.5 | 5 | 64.5 |
| D Series | 0.5 | 0 | 46.75 |
| | 0.5 | 1 | 54.75 |
| | 0.5 | 2 | 58.0 |
| | 0.5 | 3 | 62.0 |
| | 0.5 | 4 | 65.0 |
| | 0.5 | 5 | 67.0 |
| 2% Perfume Oil | | | |
| A Series | 2 | 0 | 26.25 |
| | 2 | 1 | 40.0 |
| | 2 | 2 | 39.5 |
| | 2 | 3 | 40.5 |
| | 2 | 4 | Split |
| | 2 | 5 | 40.0 |
| B Series | 2 | 0 | 36.5 |
| | 2 | 1 | 48.0 |
| | 2 | 2 | 51.0 |
| | 2 | 3 | 52.0 |
| | 2 | 4 | 51.0 |
| | 2 | 5 | 52.0 |
| C Series | 2 | 0 | 41.0 |
| | 2 | 1 | 53.0 |
| | 2 | 2 | 56.0 |
| | 2 | 3 | 57.0 |
| | 2 | 4 | 56.5 |
| | 2 | 5 | 59.5 |
| D Series | 2 | 0 | 46.0 |
| | 2 | 1 | 51.0 |
| | 2 | 2 | 58.0 |
| | 2 | 3 | 58.5 |
| | 2 | 4 | Split |
| | 2 | 5 | 66.0 |

The foregoing data demonstrate that the adverse effect of increasing perfume oil content on stick setting point and physical condition can be offset by increasing sodium stearate or by adding sodium chloride to the formulation. The latter is preferred, however, because sodium chloride is less expensive than sodium stearate, and its presence has a greater effect on increasing the setting point of the composition.

The foregoing examples are merely illustrations of the type of cosmetic product which can be made employing the sodium stearate-water vehicle of this invention. Still other cosmetic products will be apparent to those of ordinary skill in the art. For example, stick type insect repellants can be employed by incorporating an insect repellant compound as the active ingredient.

The setting points reported in Examples 14 and 15 were determined as follows:

(1) A heated solution of the test formulation was placed on a magnetic stirrer, with a stirring bar and a thermometer immersed in the formulation;

(2) The formulation was allowed to cool, while being stirred at a slow to moderate speed to maintain a homogenous mixture; and (3) The temperature at which the formulation became sufficiently viscous to prevent rotations of the stirring bar was taken as the setting point.

Although the foregoing description has been directed toward use of the water-sodium stearate vehicle of this invention as a vehicle for cosmetic preparations, it should be noted that the vehicle can be employed in compositions intended for other, but related applications. For example, solid room air deodorants or air "fresheners" have become of considerable importance. Such deodorants ordinarily consist of from about 1 to about 3 weight percent of a fragrance oil dispersed in a solid vehicle, typically an alcohol gel of the type used in stick-type deodorants. The solid vehicle of this invention provides an excellent low cost vehicle for such compositions.

What is claimed is:

1. In an improved cosmetic stick composition having an aqueous sodium stearate and water environment consisting essentially of:
   (1) an aqueous sodium stearate-water vehicle formed of:
     (a) 100 parts by weight of water; and
     (b) from about 1 to about 30 parts by weight of sodium stearate;
   (2) from about 0.05 to about 50 weight percent, based upon the total weight of the composition, of at least one cosmetic active ingredient intended to be deposited on human skin, which ingredient is stable in the aqueous alkaline environment provided by said sodium stearate-water vehicle; wherein the improvement comprises
   (3) sodium chloride in an amount of from about 0.5 weight percent to about 5 weight percent, based upon the water-sodium stearate vehicle, to increase the setting point of said composition and to inhibit syneresis.

2. A composition according to claim 1 wherein the amount of sodium stearate is from about 2 to about 20 parts by weight.

3. A composition according to claim 1 wherein said active ingredient is selected from the group consisting of bacteriostats, fungistats, pigments, dyes, perfumes, emollients, humectants, ultraviolet absorbers, talc and insect repellants.

4. A composition according to claim 1 having a setting point in the range of from about 50° C. to about 60° C.

5. A deodorant stick composition according to claim 1 wherein said active ingredient is a bacteriostat in an amount of from 0.05 to about 0.5 weight percent of the total composition, and the amount of sodium stearate is from about 5 to about 15 parts by weight.

6. A deodorant stick composition according to claim 5 wherein the amount of sodium stearate is from about 9 to about 12 parts by weight and the amount of bacteriostat is from about 0.075 to about 0.2 weight percent of the total composition.

7. A perfume stick composition according to claim 1 containing from about 5 to about 15 parts by weight of sodium stearate and from about 2 to about 8 weight percent of a perfume concentrate.

8. A sun stick composition according to claim 1 containing from about 5 to about 15 parts by weight of sodium stearate and from about 0.5 to about 5 weight percent of an ultraviolet absorber.

9. An emollient-humectant stick composition according to claim 1 containing from about 5 to about 15 parts by weight of sodium stearate and from about 2 to about 10 weight percent of an emollient or humectant.

10. A make-up stick composition according to claim 1 containing from about 5 to about 15 parts by weight of sodium stearate and from about 1 to about 10 weight percent of a pigment.

11. A talc stick composition according to claim 1 containing from about 1 to about 30 parts by weight of sodium stearate and from about 10 to 100 parts by weight of talc per 100 parts water.

12. A talc stick composition according to claim 11 containing from about 8 to about 20 parts by weight of sodium stearate and from about 10 to about 50 parts of talc.

13. A hand lotion stick composition according to claim 1 containing from about 5 to about 15 parts of sodium stearate and from about 5 to about 15 weight percent of lanolin or a lanolin derivative.

14. A cosmetic stick composition according to claim 1 additionally including a polyhydroxyl compound in an amount of from about 0.5 to about 10 weight percent of the total composition.

15. A cosmetic stick composition according to claim 14 having a setting point in the range of from about 50° C. to about 60° C.

16. A cosmetic stick composition according to claim 2 additionally including polyhydroxyl compound in an amount of from about 1 to about 8 weight percent of the total composition.

17. A deodorant stick composition according to claim 14 wherein said active ingredient is a bacteriostat is an amount of from 0.05 to about 0.5 weight percent of the total composition, and the amount of sodium stearate is from about 2 to about 15 parts by weight.

18. A deodorant stick composition according to claim 16 wherein the amount of sodium stearate is from about 9 to about 12 parts by weight and the amount of bacteriostat is from about 0.075 to about 0.2 weight percent of the total composition.

19. A perfume stick composition according to claim 14 containing from about 5 to about 15 parts by weight of sodium stearate and from about 2 to about 8 weight percent of a fragrance concentrate.

20. A sun stick composition according to claim 14 containing from about 5 to about 15 parts by weight of sodium stearate and from about 0.5 to about 5 weight percent of an ultraviolet absorber.

21. An emollient-humectant stick composition according to claim 14 containing from about 5 to about 15 parts by weight of sodium stearate and from about 2 to about 10 weight percent of an emollient or humectant.

22. A make-up stick composition according to claim 14 containing from about 5 to about 15 parts by weight of sodium stearate and from about 1 to about 10 weight percent of a pigment.

23. A talc stick composition according to claim 14 containing from about 1 to about 30 parts by weight of sodium stearate and from about 10 to 100 parts by weight of talc per 100 parts water.

24. A talc stick composition according to claim 23 containing from about 8 to about 20 parts by weight of sodium stearate and from about 10 to about 50 parts of talc.

25. A hand lotion stick composition according to claim 14 containing from about 5 to about 15 parts by weight of sodium stearate and from about 5 to about 15 weight percent of lanolin or a lanolin derivative.

26. A composition according to claim 1 wherein the amount of sodium chloride does not exceed the amount of sodium stearate.

27. A composition according to claim 1 wherein the amount of sodium chloride is from about 1.5 weight percent to about 2.5 weight percent.

* * * * *

UNITED STATES PATENT AND TRADEMARK OFFICE
CERTIFICATE OF CORRECTION

PATENT NO. : 4,322,400
DATED : March 30, 1982
INVENTOR(S) : Edward R. Yuhas

It is certified that error appears in the above—identified patent and that said Letters Patent is hereby corrected as shown below:

Column 5, line 35, change "40°C" to -- 4°C --.

Signed and Sealed this

Third Day of August 1982

[SEAL]

Attest:

GERALD J. MOSSINGHOFF

*Attesting Officer*  *Commissioner of Patents and Trademarks*